United States Patent [19]

Joo

[11] Patent Number: 5,690,940
[45] Date of Patent: Nov. 25, 1997

[54] LOW PATHOGENCITY PRRS LIVE VIRUS VACCINES AND METHODS OF PREPARATION THEREOF

[75] Inventor: Han Soo Joo, New Brighton, Minn.

[73] Assignee: Regents of the University of Minnesota, Minneapolis, Minn.

[21] Appl. No.: 493,265

[22] Filed: Jun. 21, 1995

[51] Int. Cl.$^6$ .............................. C12N 15/38; C12N 7/01; C07K 14/055
[52] U.S. Cl. .................... 424/229.1; 435/239; 435/235.1
[58] Field of Search .......................... 424/229.1, 204.1; 435/235.1, 239

[56] References Cited

PUBLICATIONS

Collins et al 1992 J. Vet Diagn Invest. 4: 117–126.
Mardassi et al 1995 Arch Virol 140: 1405–1418.

*Primary Examiner*—Lila Feisee
*Assistant Examiner*—Julie E. Reeves
*Attorney, Agent, or Firm*—Hovey, Williams, Timmons & Collins

[57] ABSTRACT

Live or modified live PRRS vaccines for administration to swine are provided which are of low virulence and confer effective immunity against PRRS. The preferred vaccines include virus isolates having average plaque diameters of less than about 2 mm and low pathogenicity. A preferred vaccine includes a small plaque diameter strain, ATCC Accession No. VR2509. The vaccines of the invention may be administered to breeding females or gilts and to weaned piglets, and is effective to immunize the swine against both the respiratory and reproductive forms of the disease.

12 Claims, 1 Drawing Sheet

LOW PATHOGENCITY PRRS LIVE VIRUS VACCINES AND METHODS OF PREPARATION THEREOF

BACKGROUND OF THE INVENTION

1. Field of the Invention

The present invention is broadly concerned with low pathogenicity live virus vaccines for administration to swine in order to confer effective immunity in the swine against porcine reproductive and respiratory syndrome (PRRS) virus infections. More particularly, the invention pertains to such live vaccines, together with methods of immunizing swine against PRRS virus and methods of preparing such vaccines. A new, substantially isolated and purified PRRS virus of low pathogenicity, ATCC Accession No. VR2509, also forms a part of the invention.

2. Description of the Prior Art

PRRS has emerged in the last several years as an important viral disease of swine. PRRS causes severe reproductive failure in pregnant sows, manifested in the form of premature farrowings, increased numbers of stillborn, mummified and weak-born pigs, decreased farrowing rates and delayed return to estrus. The acute reproductive signs of PRRS generally lasts 2–4 months on affected farms, but the respiratory problems of the disease may continue for many years, causing significant production losses. Several studies on the pathogenesis of PRRS virus infection in late term (77–95 days of gestation) pregnant sows/gilts have been reported. In each such study, the ability of PRRS virus to cause transplacental infection and fetal pathogenicity was demonstrated. However, the fetal pathogenicity was not obvious in sows during mid-gestation, and mid-gestation fetuses infected in utero remained grossly normal.

Under field conditions, there are some farms that have not shown either acute reproductive problems or the chronic respiratory form of the disease but are serologically positive for PRRS. The bases for lack of clinical signs of the disease in such instances are not well understood. It has been suggested that PRRS virus strains of low pathogenicity may exist and that these are responsible for infections in swine populations not exhibiting clinical symptoms of PRRS. Different researchers have reported a number of PRRS virus isolates. All have been shown to have RNA and lipid-containing envelopes, but no hemagglutinating ability to erythrocytes of different animal species.

SUMMARY OF THE INVENTION

The present invention overcomes the problems outlined above, and provides improved live or modified live PRRS vaccines for administration to swine. The vaccines of the invention comprise a sufficient quantity of live or modified live virus to confer effective immunity in the swine against virulent wild-type PRRS infection. As used herein, "effective immunity" refers to the ability of the vaccine to prevent swine PRRS infections which yield substantial clinical signs of the disease. That is to say, the immunized swine may or may not be serologically positive for PRRS, but do not exhibit any substantial clinical symptoms.

In preferred forms, the vaccines of the invention include a new live virus, designated MN-Hs, which has been deposited in the American Type Culture Collection (ATCC), 12301 Parklawn Drive, Rockville, Md. 20852, and has been accorded ATCC Accession No. VR2509. This virus has been shown to be substantially avirulent and confers effective immunity. The vaccines hereof may be administered to breeding females, gilts, boars or weaned piglets, and such administration may be by any convenient means such as intramuscular injection or oral-nasal administration. Generally, doses of the vaccine would contain from about $10^4$ to about $10^8$ plaque forming units of the virus.

More generally, the invention also pertains to a method of preparing PRRS swine vaccines which involves first obtaining by plaque cloning techniques a PRRS virus strain or isolate having an average plaque diameter of less than about 2 mm, on a confluent lawn of MARC-145 cells and preparing a live vaccine from such a strain. The MARC-145 cell line has been deposited in the ATCC, and has been accorded ATCC Accession No. CRL-12219. Preferably, the vaccines of the invention consist essentially of such small plaque diameter virus which is obtained in substantially purified form. The preferred virus ATCC Accession No. VR2509 has such a small plaque diameter, and as indicated is essentially completely avirulent while conferring immunity.

DETAILED DESCRIPTION OF THE PREFERRED EMBODIMENT

Figures 1, 2, 3:
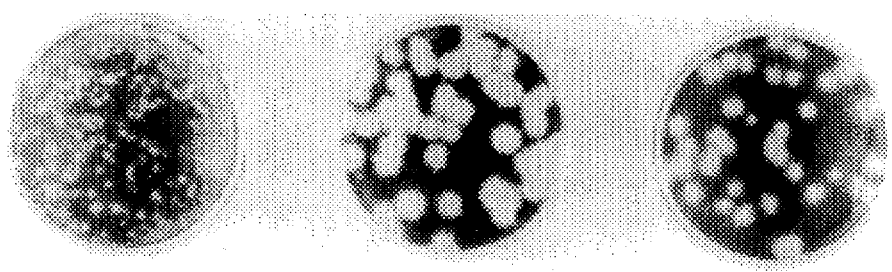
FIG. 1 is a photograph illustrating plaque morphology and size of PRRS virus isolate MN-Hs (<2 mm) on MARC-145 cell line.
FIG. 2 is a photograph illustrating plaque morphology and size of PRRS virus isolate MN-HI (3–5 mm) on MARC-145 cell line.
FIG. 3 is a photograph illustrating plaque morphology and size of PRRS virus isolate MN-W (2–3 mm) on MARC-145 cell line.

The following examples set forth the preferred techniques for isolation, identification and cloning of low pathogenicity PRRS virus strains, as well as a preferred technique for the production of vaccines therefrom; it is to be understood that this information is provided by way of illustration only, and nothing therein should be taken as a limitation upon the overall scope of the invention. The references mentioned are incorporated by reference herein.

EXAMPLE 1

Summary

In this example, the pathogenesis of a small plaque variant (MN-Hs) of porcine reproductive and respiratory syndrome (PRRS) virus was investigated in pregnant sows. The MN-Hs strain was initially cloned from MN-H virus that was a mixture of small and large plaque (MN-HI) viruses. In the first experiment to compare the fetal pathogenicity, 2 pregnant sows each at 86 days of gestation were inoculated intranasally with MN-Hs, MN-HI, a field isolate (MN-W), and cell culture medium (controls), respectively. All sows were allowed to farrow at their terms except for the control sows. Infected sows were viremic on day 7 post-inoculation (PI) and seroconverted on day 14 PI by an indirect fluorescent antibody (IFA) test. Two sows infected with MN-Hs virus delivered 14 live and 5 dead pigs, whereas 2 sows infected with MN-HI virus farrowed 0 live and 25 dead pigs. Two sows inoculated with MN-W farrowed 10 live and 20 dead piglets. Two control sows had 16 normal fetuses at slaughter on 107 days of gestation. Virus was isolated from 16 (66.7%) of 24 liveborn, 9 (64.3%) of 14 stillborn and 3 (12.0%) of 25 mummified pigs of the 6 infected sows. Six of 13 sera from stillborn pigs of 4 MN-HI or MN-W infected sows had PRRS virus antibody titers ranging from 1:16–1:1,024 by IFA method. In a subsequent experiment to repeat the results with MN-Hs virus, 2 pregnant sows each at 86 days of gestation were inoculated intranasally with MN-Hs, intramuscularly with MN-Hs and intranasally with a different field isolate (OVL-173), respectively, and all sows were allowed to farrow at their terms. The two sows infected intranasally and intramuscularly with MN-Hs virus farrowed 15 live with 6 dead pigs and 25 live with 5 dead pigs, respectively, whereas 2 sows infected with OVL-173 delivered 6 live born and 24 dead pigs. These results suggest that pathogenicity of PRRS virus for swine fetuses differs among the virus isolates, and MN-Hs strain of PRRS virus is a mild pathogenic virus. Detection of PRRS virus antibody in sera of stillborn pigs was found to be a useful method for the diagnosis of fetal infection.

Materials and Methods

Virus and cell culture. Three different PRRS virus isolates were used in this study. An isolate MN-H was derived from the serum of a healthy nursery pig in a farm with subclinical PRRS sign. The MN-H virus was initially a mixture of virus populations with varying plaque sizes. A small (MN-Hs) and a large (MN-HI) plaque virus were cloned separately from the MN-H virus, and each virus was plaque purified four times for the first experiment and six additional times for the subsequent experiment by a plaque cloning method in accordance with Kim et al., Am. J. Vet. Res., 52:1649–1652 (1991). In each such plaque passage, confluent MARC-145 (a permissive clone derived from an African green monkey kidney cell line (MA-104)) cell monolayers were grown in 60 mm×15 mm petri dishes (the cells were maintained in Eagles minimum essential medium (MEM) supplemented with 3% fetal calf serum (FCS), 0.15% sodium carbonate, and antibiotics, (Kim et al., Arch. Virol, 133:477–483 (1993)) and were inoculated with a respective virus. The cultures were incubated for 60 min. at 37° C. whereupon the inoculum was removed and the cultures were washed once with MEM. Thereafter, a 5 ml aliquot of liquid culture medium was added to each dish, consisting of equal volume of 2X MEM and 1.6% boiled Noble agar (Difco Laboratories) supplemented with 50 µg of diethylaminoethyl (DEAE)-dextran/ml. The plates were further incubated for 5 days at 37° C. in a $CO_2$ incubator. At the end of the incubation period, the plaque cultures were visualized by adding thereto 3 ml of PBS supplemented with 1% neutral red. Selected plaques were cloned by picking with a sterile Pasteur pipette and were passed by inoculation onto uninfected MARC-145 cell monolayers. For a permanent staining, the agar was removed carefully and the cell monolayers were stained with 2 ml of 1% crystal violet in 20% ethanol for 10 min. The plates were rinsed with tap water to facilitate examination of the plaques.

PRRS virus MN-W was isolated from the serum of sick sows of a farm with typical acute PRRS signs, and OVL-173 was obtained from Oxford Veterinary Laboratories, Worthington, Minn.

Animal and experimental design. Pregnant sows at about 80 days of gestation were purchased from a farm that had no history of clinical or serological evidence of PRRS virus infection. Sows had been vaccinated twice a year against porcine parvovirus (PPV) and Leptospira spp. on the farm. Accurate breeding dates of each sow were obtained. Following purchase, each sow was housed separately in an isolation room at the University of Minnesota. At 86 days of gestation, two sows each were inoculated intranasally with MN-Hs, MN-HI and MN-W virus (2 ml, $10^{5.0-5.5}$ $TCID_{50}$/ml), respectively. The remaining two sows were inoculated with cell culture medium and served as controls. Serum samples from each sow were collected at intervals for virus isolation and serology. Six infected sows were allowed to farrow naturally, and two control sows were slaughtered at 107 days of gestation for examination of the fetuses. At farrowing, blood and lung samples from live and stillborn piglets and thoracic fluids from mummified fetuses were collected for virus isolation and serology. In the second experiment, the MN-Hs virus was plaque purified six additional times prior to inoculation. Two pregnant sows each at 86 days of gestation were inoculated intranasally with MN-Hs, intramuscularly with MN-Hs and intranasally with a different field isolate (OVL-173), and all sows were allowed to farrow at their terms. At farrowing, crown-rump lengths of mummified or stillborn fetuses were measured to estimate the time of death (Marrable et al., J. Agric. Sci., 69:443–447 (1967)). Blood and lung samples were collected and analyzed as described in the first experiment.

Virus isolation and serology. For virus isolation, each serum sample or supernatant of the lung homogenate was placed on 24-well plate wells, and MARC-145 cells (1–2× $10^5$ cells/ml) suspended in MEM supplemented with 3% FCS was added. The cultures were observed for cytopathic effects (CPE) typical of PRRS virus for 5–7 days. The plates were frozen and thawed twice, and the supernatants were inoculated in 96-well microplate wells with fresh MARC-145 cell suspension and incubated for 3–4 days. Evidence for virus infection was examined by observations of both CPE and specific fluorescence using a PRRS virus reference positive swine serum.

Sera from the sows and pigs were tested for antibody by an indirect fluorescent antibody (IFA) method (Yoon et al., J. Vet. Diag. Invest., 4:144–147 (1992)). The 96-well test plates were prepared using MARC-145 line cells. Some of the sera were tested for antibody to PPV by hemagglutination inhibition (HI) test as described previously (Joo et al., Aust. Vet. J., 52:422–424 (1976)).

Results

PRRS virus isolates showed different plaque sizes at initial isolation. The MN-H isolate was cloned into two different populations of MN-Hs and MN-HI by their plaque sizes. After cloning, the respective plaque sizes for MN-Hs and MN-HI consistently ranged from <2 mm and 3–5 mm in diameters, while those of MN-W were 2–3 mm (see Figures).

No major clinical signs were observed in the sows following infection with PRRS virus isolates, other than mild anorexia detected in sows 112 and 153 for 5 days post inoculation (PI). Virus was isolated from serum samples of six of the six sows seven days PI and one of the six sows 14 days PI. High antibody titers were detected in all inoculated sows 14 days PI, as set forth in Table 1.

TABLE 1

Viremia and antibody response in 86-day pregnant sows following experimental infection with PRRS virus isolates

| Sow No. | Virus infected | Days after inoculation | | | | |
|---|---|---|---|---|---|---|
| | | 0 | 7 | 14 | 21 | 28 |
| 17 | MN-Hs | –/–* | +/– | –/1,024 | –/1,024 | –/256 |
| 53 | MN-Hs | –/– | +/– | –/1,024 | –/1,024 | –/1,024 |
| 153 | MN-HI | –/– | +/– | –/1,024 | –/1,024 | –/256 |
| 147 | MN-HI | –/– | +/– | –/1,024 | –/1,024 | –/1,024 |
| 68 | MN-W | –/– | +/– | –/1,024 | –/1,024 | –/1,024 |
| 112 | MN-W | –/– | +/– | +/1,024 | –/1,024 | –/1,024 |
| 124 | Control | –/– | –/– | –/– | –/– | –/– |
| 95 | Control | –/– | –/– | –/– | –/– | –/– |

*Virus isolated from blood/Reciprocals of antibody titers measured by IFA

The farrowing results of each sow are summarized in Table 2. A marked difference was observed in the farrowing results of the sows infected with different virus variants. Two sows infected with MN-Hs virus farrowed 14 live born, 1 stillborn and 4 mummified pigs, while 2 sows infected with MN-HI virus produced 0 live born, 6 stillborn and 19 mummified pigs. Two sows inoculated with MN-W virus farrowed 10 live born, 7 stillborn and 13 mummified pigs. Two control sows had 26 normal fetuses at slaughter on 107 days of gestation. In experiment II, two sows infected intranasally and intramuscularly with MN-Hs virus farrowed 15 live with 6 dead pigs and 25 live with 5 dead pigs, respectively, whereas 2 sows infected with OVL-173 delivered 6 live born and 24 dead pigs (Table 2). When comparing farrowing results of experiments I and II, 6 MN-Hs infected and 6 MN-HI, MN-W or OVL-173 infected sows farrowed 54 live (77.1%) with 16 dead pigs and 16 live (18.8%) with 69 dead pigs, respectively. Except for the 3 mummified fetuses from sows 147 and 176, CR lengths of all mummified or stillborn fetuses were ≧24 cm (Table 2), indicating the estimated death time at ≧95 days of gestation.

TABLE 2

Farrowing results and virus isolation from 86-day gestation sows infected with different PRRS virus isolates

| | Sows | | | Fetuses | | | | |
|---|---|---|---|---|---|---|---|---|
| No. | Days[a] | Virus/route | Total | LB | SB | M | Cr Length range[b] | Virus isolation[c] |
| | | Experiment I | | | | | | |
| 17 | 115 | MN-Hs/IN | 9 | 6 | 0 | 3 | 27–32 | 6/9 |
| 53 | 113 | MN-Hs/IN | 10 | 8 | 1 | 1 | 25–38 | 6/10 |
| 153 | 114 | MN-HI/IN | 13 | 0 | 2 | 11 | 24–32 | 2/11 |
| 147 | 112 | MN-HI/IN | 12 | 0 | 4 | 8 | 18–30 | 3/7 |
| 68 | 112 | MN-W/IN | 15 | 8 | 3 | 4 | 25–28 | 5/15 |
| 112 | 118 | MN-W/IN | 15 | 2 | 4 | 9 | 24–31 | 6/11 |
| 124 | 107[d] | Control | 14 | 14 | — | — | ND | 0/14 |
| 95 | 107[d] | Control | 12 | 12 | — | — | ND | 0/12 |
| | | Experiment II | | | | | | |
| 155 | 115 | MN-Hs/IN | 11 | 7 | 3 | 1 | 28–35 | 8/11 |
| 49 | 114 | MN-Hs/IN | 10 | 8 | 2 | 0 | 34–37 | 9/10 |
| 176 | 112 | MN-Hs/IM | 15 | 12 | 2 | 1 | 15–36 | 3/15 |
| 110 | 113 | MN-Hs/IM | 15 | 13 | 2 | 0 | 32–34 | 2/15 |
| 800 | 108 | OVL-173/IN | 12 | 1 | 9 | 2 | 27–28 | 1/12 |
| 44 | 108 | OVL-173/IN | 18 | 5 | 10 | 3 | 26–29 | 10/18 |

[a]Gestational day at farrowing or slaughter
[b]Crown-Rump length (cm) of mummified or stillborn fetuses
[c]No. of samples virus isolated/No. of sample tested
[d]Sows were slaughtered at 107 days of gestation to examine the fetuses LB; Live born, SB; Stillbirth, M; Mummified, IN; Intranasal, IM; Intramuscular, ND; Not determined Virus was isolated from one or more fetuses in every litter of infected sows. Virus isolation results from individual pigs from six infected sows in Experiment I showed that approximately half of the fetuses (28 of 63 pigs) examined were positive by virus isolation. Among the pigs tested for the presence of virus, 16 (66.7%) of 24 live born pigs, 9 (64.3%) of 14 stillborn pigs, and 3 (12.0%) of 25 mummified pigs were virus positive. Of 28 pigs virus positive from their serum samples, 10 pigs were negative for virus when their lung samples were tested for virus isolation.

Sera from stillborn pigs of sows 153, 147, 68 and 112 were tested for antibodies to PRRS virus by IFA and to PPV by HI, and the results are shown in Table 3. Six of 13 sera from the stillborn pigs and 2 of 25 thoracic fluids from the mummified pigs had PRRS virus antibody. The IFA titers ranged from 1:16–1:1,024, while none of the sera had antibody to PPV. 1.5 Thirteen of 14 live born pigs from sows 17 and 53 had antibodies to both PRRS virus (IFA titers 1:64–1:1,024) and PPV (HI titers 1:512–1:16,384).

TABLE 3

Detection of antibodies to PRRS virus and PPV in sera from stillborn pigs of sows infected with PRRS virus

| Sow No. | Virus infected | History of litter | Fetuses tested | PRRSV IFA | PPV HI |
|---|---|---|---|---|---|
| 153 | MN-HI | 0 LB, 2 SB, 11 M | SB (32)[a] | <4[b] | <8[b] |
| | | | SB (27) | 256 | <8 |
| 147 | MN-HI | 0 LB, 4 SB, 8 M | SB (30) | <4 | <8 |
| | | | SB (30) | 1,024 | <8 |
| | | | SB (29) | <4 | <8 |
| | | | SB (28) | <4 | <8 |
| 68 | MN-W | 8 LB, 3 SB, 4 M | SB (27) | <4 | <8 |
| | | | SB (25) | 16 | <8 |
| | | | SB (28) | <4 | <8 |
| 112 | MN-W | 2 LB, 4 SB, 9 M | SB (31) | >4 | <8 |
| | | | SB (29) | 256 | <8 |
| | | | SB (26) | 256 | |
| | | | SB (24) | 16 | NT |

[a]Crown-rump length (cm)
[b]Reciprocals of IFA or HI titer
LB; Live born,
SB; Stillbirth,
M; Mummification Discussion The present study confirmed the ability of different PRRS virus isolates to cause transplacental infection and pathogenic effects on the fetuses of sows in the late gestation. However, there was an obvious difference in the pathogenicity between the PRRS virus isolates. When multiparous sows were inoculated intranasally with PRRS virus ATCC-VR 2332 on day 93 of gestation, (Christianson, W. T. et al.; Can. J. Vet Res., 57:262–268 (1993)), they delivered an average of 5.8 live piglets and 6.0 dead fetuses per liter. In the present study, 6 sows were infected with MN-HI or 2 field viruses farrowed an average of 2.7 live and 11.5 dead pigs per litter, and thus these viruses are considered as highly virulent. The pathogenicity between ATCC-VR 2332 and the virulent viruses used in this study was different. This may be due to the gestational ages at the time of infection as ATCC-VR 2332 virus was infected 7 days later. Meanwhile, 6 sows infected with MN-Hs delivered an average of 9.0 live born and 2.7 dead pigs per litter. These results are markedly different from those for virulent viruses, indicating that the MN-Hs virus is a mild pathogenic strain.

It is interesting that an obvious difference was observed in the farrowing results of sows infected with MN-Hs and MN-HI viruses that were from the same origin. Under the same conditions, MN-Hs and MN-HI viruses caused 5 and 25 born dead pigs (p <0.005), respectively. With the present results, it can be concluded that pathogenicity of MN-Hs and MN-HI is significantly different, one being a mild strain and another a highly pathogenic virus.

Virus isolation from PRRS virus infected litters was relatively easy, and virus was isolated in similar rate between live and stillborn pigs. Because virus could not be recovered from all of the pigs in an infected litter, virus isolation for a diagnostic purpose should be attempted from at least 2 or more piglets per litter. Also, it is found that virus isolation was more conveniently carried out from serum than from lung tissue samples.

In the litters of sows infected with virulent virus, one or more stillborn pigs had detectable antibody specific to PRRS virus. These results suggest that antibody detection from stillborn or presucked piglets can be a useful method for the diagnosis of PRRS virus infection in the abnormal litters.

This method would be worthwhile in the laboratories where the virus isolation techniques and facilities are not available. In the present study, 6 of 13 stillborn pigs had positive antibody titers to PRRS virus but not to PPV, assuring that the antibodies detected are of fetal origin and are due to PRRS virus.

It is not known why some herds infected with PRRS virus do not develop clinical signs. It has been experienced that herds with a high health status prior to PRRS virus infection demonstrated a milder clinical response, as compared to those with a lower level of health. The prevailing health status, along with strain differences demonstrated in this study are possible explanations for apparent differences in clinical presentation. Additionally, it may be postulated that an interaction between small and large plaque viruses may occur within a host animal and modify the pathogenicity. This may be true, if we consider that there was a lack of reproductive problems in the farm, where MN-H virus was isolated, despite a highly pathogenic PRRS virus MN-HI was present in the farm.

EXAMPLE 2

Preferred vaccines in accordance with the invention can be administered to breeding gilts, sows, boars or weaned piglets. The administration can be intramuscular or oral-nasal and can be given at any time. However, vaccinations are preferred for breeding females before mating to protect the entire pregnancy period, and shortly after weaning for young pigs to protect their late nursery, grower and finishing stages.

Generally, the vaccines of the invention are given in 2 ml doses which contain from about $10^4$ to about $10^8$ plaque forming units (PFU), and more preferably about $10^6$ PFU. The immunity will last at least one pregnancy period in the case of breeding females, whereas post-weaning vaccination of young piglets will confer immunity for protection throughout the finishing period. Preferred vaccines in accordance with the invention can give a wide range of cross-protection.

Vaccines in accordance with the invention can include live or modified live (attenuated) virus, as well as conventional carriers, stabilizers and/or adjuvants.

I claim:

1. A vaccine comprising a virus having the designation ATCC VR2509.
2. The vaccine of claim 1, wherein the virus is live.
3. The vaccine of claim 1, wherein a dose of the vaccine contains from $10^4$ to $10^8$ PFU.
4. A method of immunizing a swine against North American porcine reproductive and respiratory syndrome, comprising the step of administering to the swine the vaccine of claim 1.
5. The method of claim 4, wherein the virus is live.
6. The method of claim 4, wherein the swine is a mature breeding female.
7. The method of claim 4, wherein the swine is a piglet.
8. The method of claim 4, wherein the vaccine is administered intramuscularly, intranasally, or orally.
9. A vaccine comprising a North American porcine reproductive and respiratory syndrome virus (PRRSV) strain, wherein the strain gives plaques having an average diameter of less than 2 mm when the plaques are obtained by a method comprising the steps of:

(a) inoculating an aliquot of cells with the strain, wherein the cells have the designation ATCC CRL-12219, wherein the aliquot is obtained from a confluent monolayer of the cells maintained in Eagle's minimum essential medium supplemented with 3% fetal calf serum and 0.15% sodium carbonate, wherein the aliquot includes 1–2 X $10^5$ cells per ml of Eagle's minimum essential medium supplemented with 3% fetal calf serum and 0.15% sodium carbonate;
   (b) incubating the aliquot at 37° C. for 60 minutes;
   (c) removing the inoculum from the aliquot;
   (d) washing the aliquot with Eagle's minimum essential medium;
   (e) resuspending the aliquot in 5 ml of 2X Eagle's minimum essential medium and 1.6% boiled Noble agar supplemented with 250 µg of diethylaminoethyl (DEAE)-dextran;
   (f) plating the aliquot; and
   (g) further incubating the aliquot at 37° C. for 5 days in a $CO_2$ incubator to give the plaques.

10. The vaccine of claim 9, wherein the vaccine comprises a live North American porcine reproductive and respiratory syndrome virus (PRRSV) strain.

11. An isolated and purified North American porcine reproductive and respiratory Syndrome virus (PRRSV) strain, wherein the strain has the designation ATCC VR2509.

12. An isolated and purified North American porcine reproductive and respiratory syndrome virus (PRRSV) strain, wherein the strain gives plaques having an average diameter of less than 2 mm when the plaques are obtained by a method comprising the steps of:

(a) inoculating an aliquot of cells with the strain, wherein the cells have the designation ATCC CRL-12219, wherein the aliquot is obtained from a confluent monolayer of the cells maintained in Eagle's minimum essential medium supplemented with 3% fetal calf serum and 0.15% sodium carbonate, wherein the aliquot includes 1–2 X $10^5$ cells per ml of Eagle's minimum essential medium supplemented with 3% fetal calf serum and 0.15% sodium carbonate;
   (b) incubating the aliquot at 37° C. for 60 minutes;
   (c) removing the inoculum from the aliquot;
   (d) washing the aliquot with Eagle's minimum essential medium;
   (e) resuspending the aliquot in 5 ml of 2X Eagle's minimum essential medium and 1.6% boiled Noble agar supplemented with 250 µg of diethylaminoethyl (DEAE)-dextran;
   (f) plating the aliquot; and
   (g) further incubating the aliquot at 37° C. for 5 days in a $CO_2$ incubator to give the plaques.

* * * * *